(12) United States Patent

Tivig et al.

(10) Patent No.: US 9,607,495 B2
(45) Date of Patent: Mar. 28, 2017

(54) DEVICE FOR CONTROLLING THE ALARM LIMIT OF AN ALARM DEVICE

(75) Inventors: Gerhard Tivig, Nufringen (DE); Rolf Neumann, Calw (DE); Michael Mathias Spaeth, Stuttgart (DE); Harald Greiner, Nufringen (DE); Guenter Gegner, Tuebingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 579 days.

(21) Appl. No.: 13/994,140

(22) PCT Filed: Dec. 14, 2011

(86) PCT No.: PCT/IB2011/055665
§ 371 (c)(1),
(2), (4) Date: Jun. 14, 2013

(87) PCT Pub. No.: WO2012/080963
PCT Pub. Date: Jun. 21, 2012

(65) Prior Publication Data
US 2013/0263855 A1 Oct. 10, 2013

(30) Foreign Application Priority Data
Dec. 17, 2010 (EP) .................................. 10195673

(51) Int. Cl.
*A61M 11/00* (2006.01)
*G08B 21/02* (2006.01)
(Continued)

(52) U.S. Cl.
CPC ............ *G08B 21/02* (2013.01); *A61B 5/4839* (2013.01); *A61B 5/4848* (2013.01);
(Continued)

(58) Field of Classification Search
CPC ........ A61M 2230/432; A61M 16/0051; A61M 2016/0036; A61M 2205/502;
(Continued)

(56) References Cited

U.S. PATENT DOCUMENTS 4,776,339 A 10/1988 Schreiber
6,807,965 B1 10/2004 Hickle
(Continued)

FOREIGN PATENT DOCUMENTS

CN 1891170 1/2007
EP 1721571 A2 11/2006

OTHER PUBLICATIONS

Boostii; Which oxygen saturation level should we use for very premature infants? A randomised controlled trial; 2006; NHMRC Clinical Trials Centre; University of Sydney, NSW; 24 pages.
(Continued)

*Primary Examiner* — Steven Douglas

(57) ABSTRACT

A controlling device (110) is configured for controlling a state of an alarm limit of an alarm device (108). The alarm device (108) is configured for generating an alarm signal in association with a monitored physiological parameter of a patient. The alarm limit triggers the generation of the alarm signal. In order to automatically control the state of the alarm limit, the controlling device (110) comprises a receiving unit (146) configured for receiving information indicating an administration of a treatment to the patient, a determining unit (148) configured for determining whether the treatment is administered to the patient based on the received information, and a controlling unit (150) configured for controlling the state of the alarm limit based on a result of the determination of the determining unit (148).

20 Claims, 2 Drawing Sheets

(51) Int. Cl.
  *A61B 5/00* (2006.01)
  *A61M 16/00* (2006.01)
  *A61M 16/10* (2006.01)
  *G06F 19/00* (2011.01)

(52) U.S. Cl.
  CPC ........ *A61M 16/0051* (2013.01); *A61M 16/10* (2013.01); *G06F 19/3406* (2013.01); *G06F 19/3418* (2013.01); *G06F 19/3468* (2013.01); *A61M 2202/0208* (2013.01); *A61M 2205/502* (2013.01); *A61M 2205/584* (2013.01); *A61M 2230/06* (2013.01); *A61M 2230/205* (2013.01); *A61M 2230/30* (2013.01); *A61M 2230/42* (2013.01); *A61M 2230/432* (2013.01); *A61M 2230/50* (2013.01)

(58) Field of Classification Search
  CPC .......... A61M 5/1723; A61M 2230/205; A61M 2202/0208; A61M 2205/18; A61M 2230/30; A61M 16/10; A61M 2205/584; A61M 2230/06; A61M 2230/42; G08B 21/02; A61B 5/4839; A61B 5/4848; G06F 19/3406; G06F 19/3418; G06F 19/3468
  USPC .......................... 128/204.18, 204.21, 204.23
  See application file for complete search history.

(56) References Cited

U.S. PATENT DOCUMENTS

2009/0241958 A1* 10/2009 Baker, Jr. .......... A61M 16/0051
                                                       128/204.23
2010/0026510 A1    2/2010 Kiani et al.

OTHER PUBLICATIONS

NICU Specific Policies; Pulse Oximetry; Jul. 1992; Cardiopulmonary Services; Proc. 17:23. 2 pages.

* cited by examiner

DEVICE FOR CONTROLLING THE ALARM LIMIT OF AN ALARM DEVICE

FIELD OF THE INVENTION

The invention relates to a controlling device for controlling a state of an alarm limit of an alarm device.

Further, the invention relates to a patient monitoring apparatus for monitoring a physiological parameter of a patient.

BACKGROUND OF THE INVENTION

It is commonly known that a patient monitoring apparatus is used for monitoring a physiological parameter of a patient, in order to continuously supervise a health state of the patient. Usually, the patient monitoring apparatus comprises an alarm device configured for providing an alarm signal in those cases in which a sensed value of the monitored physiological parameter deviates from values of a predefined interval. In particular, an alarm signal is generated in cases in which the sensed value is less than or at most equal to a lower alarm limit and in cases in which the sensed value exceeds an upper alarm limit. The lower and upper alarm limits may depend on the age of the patient, the kind of monitored physiological parameter, and general guidelines defined by a supervision unit owning or operating the patient monitoring apparatus.

It is further known that a supplementary treatment may be administered to the patient during the monitoring of the physiological parameter, in order to guarantee a proper health state of the patient and/or to improve the health state of the patient. The administration of the treatment may influence the sensed value of the monitored physiological parameter of the patient. In particular, the sensed physiological parameter value may decrease or increase, respectively, causing the sensed value of the physiological parameter to be lower than the lower alarm limit or to exceed the upper alarm limit of the alarm device of the patient monitoring apparatus, respectively. Accordingly, the lower and upper alarm limits of the alarm device may represent particularly important parameters during monitoring the patient, since the lower and upper alarm limits may represent safety relevant issues for the patient.

For example, arterial hemoglobin oxygen saturation (SpO2) of a preterm infant may be monitored using a patient monitoring apparatus during the first days after the birth of the infant, in order to guarantee a proper physical development of the infant. A deviation of the oxygen saturation value of the infant from a range of predefined values for a given time may impact the health of the infant. For example, a too low value of the oxygen saturation (hypoxemia) may result in hypoxia of the brain and other organs, which may lead to permanent damage of these organs. For a preterm infant, the lower SpO2 alarm limits of an alarm device may be defined by individual hospital definitions and may correspond to about 88%.

Further, a treatment agent in the form of supplementary oxygen may be supplied to the preterm infant, to ensure a sufficient oxygen saturation value of the infant. On the other side, supplying too much oxygen to the infant may increase the incidence of retinopathy of prematurity (ROP) and lung disease. During a time in which the infant may receive supplementary oxygen, an increased diligence of a caregiver of the infant may be required to prevent diseases of the infant resulting from too high oxygen saturation values. This may be achieved by avoiding oxygen saturation levels in the upper range (hyperoxemia). Typically this may be accomplished by using the upper SpO2 alarm limit of an alarm device. The upper SpO2 alarm limits of an alarm device may be defined by individual hospital definitions and may correspond to about 94%, a saturation value which is of no concern when the infant is breathing normal air.

By using the standard low and high SpO2 alarm limits, it may happen that nuisance alarm signals are triggered by a sensed hemoglobin oxygen saturation value exceeding the upper alarm limit although no supplementary oxygen is supplied to the infant.

In order to adapt the personal monitoring of a caregiver of the infant to the fact whether the infant is receiving oxygen or not, it is known from the medical survey "Which oxygen saturation level should we use for very premature infants? A randomized controlled trial", BOOSTII, NHMC Clinic Trials Center, 24 Aug. 2006, that the upper alarm limit of an alarm device shall be set to 94% in case a monitored infant receives supplementary oxygen and that the upper alarm limit of the alarm device shall be switched off or deactivated in cases in which the infant is exposed to air.

Further, it is known from NICU Specific policies "Pulse Oximetry", Proc17.23, issued in July 1992 and revised in July 2000, that a high Sp02 alarm is to be deactivated in cases in which the patient is exposed to room air or is a full term infant and that a high Sp02 alarm is to be set to 98% in cases in which the patient is a preterm infant and is receiving oxygen.

However, such a manual controlling of the upper alarm limit may result in a time consuming supervision of the infant, since the caregiver of the infant may have to permanently monitor the individual treatment of the infant. Further, a potential risk of health threats of the infant may be increased using the above described controlling of the state of the upper alarm limit of the alarm device.

SUMMARY OF THE INVENTION

It may be an object of the invention to provide an improved controlling of an alarm limit of an alarm device which may be used during monitoring a physiological parameter of a patient.

In order to achieve the object defined above, a controlling device for controlling a state of an alarm limit of an alarm device, and a patient monitoring apparatus for monitoring a physiological parameter of a patient are provided.

According to an exemplary aspect of the invention, a controlling device for controlling a state of an alarm limit of an alarm device is provided, wherein the alarm device is configured for generating an alarm signal in association with a monitored physiological parameter of the patient, wherein the alarm limit triggers the generation of the alarm signal, the controlling device comprising a receiving unit configured for receiving information indicating an administration of a treatment to the patient, a determining unit configured for determining whether the treatment is administered to the patient based on the received information, and a controlling unit configured for controlling the state of the alarm limit based on a result of the determination of the determining unit.

According to another exemplary aspect of the invention, a patient monitoring apparatus for monitoring a physiological parameter of a patient is provided, the patient monitoring apparatus comprising an alarm device configured for generating an alarm signal in association with the monitored physiological parameter of the patient, and a controlling device configured for controlling a state of an alarm limit of the alarm device as defined as above.

According to another exemplary aspect of the invention, a method of controlling a state of an alarm limit of an alarm device is provided, wherein the alarm device is configured for generating an alarm signal in association with a monitored physiological parameter of a patient, wherein the alarm limit triggers the generation of the alarm signal, the method comprising receiving (particularly by a receiving unit of a controlling device configured for controlling a state of an alarm limit of the alarm device) information indicating an administration of a treatment to the patient, determining whether the treatment is administered to the patient based on the received information (particularly by a determining unit of the controlling device), and controlling the state of the alarm limit based on a result of the determination of the determining unit (particularly by a controlling unit of the controlling device).

According to another exemplary aspect of the invention, a computer-readable medium is provided, in which a computer program for controlling a state of an alarm limit of an alarm device is stored, which computer program, when being executed by a processor, is configured to carry out or control a method of controlling a state of an alarm limit of an alarm device as defined above.

According to another exemplary aspect of the invention, a program element is provided, which program element, when being executed by a processor, is configured to carry out or control a method of controlling a state of an alarm limit of an alarm device as defined above.

In the context of the present application, the term "alarm limit of an alarm device" may particularly denote a numerical boundary (value) of an interval being defined in the alarm device comprising a lower numerical boundary (value) and an upper numerical boundary (value). In particular, the values of the upper and/or lower numerical boundaries of the interval may be defined or selected in accordance with a monitored physiological parameter of a patient. In particular, in cases in which a sensed physiological parameter value of the patient may correspond to a value outside of the interval, particularly may be lower than the lower alarm limit or may exceed the upper alarm limit, the alarm device may generate an alarm signal.

The term "state of the alarm limit" may particularly denote a status of an operational mode of the alarm limit and/or a value of the alarm limit associated with the generation of the alarm signal.

The term "physiological parameter" of a patient may particularly denote a physical characteristic of the patient, wherein a value of the physiological parameter may indicate a health state of the patient.

According to the exemplary aspects of the invention, an automatic control of a state of an alarm limit associated with a monitored physiological parameter of a patient may be provided. The control of the state of the alarm limit may be based on the fact whether a (particularly supplementary) treatment may be administered to the patient, which may influence the sensed value of the monitored physiological parameter of the patient.

In particular, as the state of the alarm limit of the alarm device may be automatically controlled, a monitoring of the patient may be less time-consuming in comparison with a manual controlling of the alarm limit of the alarm device. Accordingly, a caregiver of the patient may have much time at his or her disposal usable for other patients, and a hospital service may significantly improve.

In particular, basing the controlling on a result of the determination of the determining unit whether a treatment may be administered to the patient but not on a sensed value of the monitored physiological parameter of the patient may reduce an inaccurate controlling of the state of the alarm limit, since measuring errors of the sensed value may not impact the controlling of the state of the alarm limit. Thus, safety of the monitored patient may be significantly increased.

In particular, failures caused by an improper manual controlling of the alarm limit of the alarm device may significantly decrease. In particular, in cases in which a caregiver of the patient may set the alarm limit of the alarm device in a deactivated or less sensitive state and may forget to set the alarm limit of the alarm device in an activated or more sensitive state when a treatment condition of the patient may have been changed may be prevented. Thus, a safety of the patient may further increase, as potential health threats of the patient may be reduced.

In particular, the controlling device may allow for an accurate and timely adjusted control of the state of the alarm limit of the alarm device, since changes in a treatment condition of the patient may be automatically accounted for.

In particular, disturbances arising from unnecessary generations of nuisance alarm signals in cases in which no treatment may be administered to the patient may be prevented.

Next, further exemplary embodiments of the controlling device for controlling a state of an alarm limit of an alarm device will be explained. However, these embodiments also apply to the respective patient monitoring apparatus, the respective method, the respective computer-readable medium, and the respective program element.

The alarm limit may comprise at least one of a lower alarm limit of the alarm device and an upper alarm limit of the alarm device. In particular, controlling the lower and upper alarm limits may impact the interval of values between the lower and upper alarm limits which may not trigger the generation of the alarm signal.

The information may comprise at least one of an indication indicating whether the treatment may be administered to the patient, and a value indicating the amount or level of the treatment administered to the patient. In particular, the indication that the treatment is not administered to the patient may comprise zero information, for example in terms of a message having no content. Thus, the controlling device may be adapted for operating on various kinds of information, thereby being easily integratable in already existing patient monitoring apparatuses and/or central surveillance systems installed in hospitals or doctor's offices. In particular, basing the determination on the indication whether the treatment may be administered to the patient may allow for a very easy determination rule which may be less error-prone, resulting in a significantly improved accuracy of an operation of the controlling device.

In particular, the information may be generated by an another device, particularly a treatment administration device being connectable to the controlling device or the patient monitoring apparatus, based on an actual execution of the administration of the treatment to the patient and/or may be inputted by a caregiver of the patient into the controlling device, the patient monitoring apparatus and/or another input device connectable to the controlling unit. In particular, the controlling device and/or the patient monitoring apparatus may comprise a respective input unit, for example, a keyboard.

The determining unit may be configured for comparing the received value with a threshold value, wherein the determining unit may be configured for determining whether the treatment may be administered to the patient based on the comparison. Thus, an accuracy of an operation of the controlling device may be enhanced, since the determination whether the treatment may be administered to the patient or not may be based on a numerical determination. Further, a respective determination algorithm may be easily definable.

In particular, the determining unit may be configured for determining that the treatment may be administered to the patient if the received value may exceed the threshold value and for determining that the treatment may not be administered to the patient if the received value may be at most equal to the threshold value. In particular, the determining unit may be configured for determining that the treatment may be administered to the patient if the received value may not exceed the threshold value and for determining that the treatment may not be administered to the patient if the received value may exceed the threshold value. This measure may provide a particularly simple determination algorithm which may be, for example, easily integrated in already present operational functions of a controlling device.

In particular, the state of the alarm limit may comprise an activated state and a deactivated state, wherein the activated state may be associated with the alarm device generating the alarm signal and the deactivated state may be associated with the alarm device not generating the alarm signal. Thus, the controlling device may be configured for controlling whether the alarm device may generate an alarm signal or not, in order to indicate whether a sensed value of a monitored physiological parameter may be lower or may exceed an alarm limit of the alarm device.

The controlling unit may be configured for at least one of setting the alarm limit in an activated state, for setting the alarm limit in a deactivated state, or setting a value of the alarm limit to another value based on the result of the determination of the determining unit. In this context, the terms "activated state" and "deactivated state" may correspond to the terms "activated state" and "deactivated state" as explained above. In particular, setting the alarm limit in an activated state may be executed by setting a value of the alarm limit to the previously used or defined value of the alarm limit. In particular, setting the alarm limit in a deactivated state may be executed by setting a value of the alarm limit to another value. In particular, the another value selected by the controlling unit may correspond to a value which may be sufficiently different from the numerical boundary value of the alarm interval of the alarm device (for example, sufficiently high in a case of the upper alarm value or sufficiently low in a case of the lower alarm limit) such that no alarm signal may be generated. In particular, the another value of the lower alarm limit may be selected to be (about) 0.1 or a suitable numerical value corresponding to a virtual physiological parameter value of about 10%. In particular, the another value of the upper alarm limit may be selected to be (about) 1 or a suitable numerical value corresponding to a virtual physiological parameter value of about 100%. In particular, setting the value of the alarm limit to another value of the alarm limit may result in the alarm device being less or more sensitive to the monitored physiological parameter or to be sensitive to different values of the monitored physiological parameter. In particular, the controlling unit may be configured for setting the alarm limit to the another value without changing the status of the operational mode, particularly the activated or deactivated states, of the alarm limit. In particular, in a case in which the controlling device is configured for controlling the lower and upper alarm limits of the alarm device, setting the values of the lower and upper alarm limits to another values may change the interval of the alarm device which may not trigger the generation of the alarm signal. These measures may allow for adjusting a controlling of the state of the alarm limit to a particular treatment condition of the monitored patient in order to, for example, increase (particularly extend) or decrease (particularly reduce) the range of sensed values of the monitored physiological parameter which may not trigger the alarm signal, completely change the range of sensed values of the monitored physiological parameter which may not trigger the generation of the alarm signal, adjust (particularly extend) the value of the alarm limit to potentially more safety relevant, critical values of the physiological parameter, or change the value of the alarm limit to different values of the physiological parameter of a patient which may be expected owing to the treatment administered to the patient.

In particular, the controlling unit may be configured for selecting the another value based on the kind of the treatment administered to the patient, thereby the controlling unit may be enabled for automatically changing the value of the alarm limit without requiring an additional specification of the another value, for example, by a caregiver of the patient.

In particular, the value and/or the another value of the alarm limit may be definable by a caregiver prior to the use of the controlling device (for example, via an input unit of the controlling device), thereby providing a single controlling device which may be usable in association with monitoring different physiological parameters and/or with different patients.

In particular, the value and/or the another value of the alarm limit may be predetermined for the controlling device, thereby providing different controlling devices each of which may be usable in association with monitoring a different one physiological parameter and/or with a different one patient.

In particular, the controlling unit may be configured for setting the alarm limit in the activated state if the treatment may be administered to the patient and for setting the alarm limit in the deactivated state if the treatment may not be administered to the patient. Thus, an alarm signal may only be generated in those cases in which a supplementary treatment may be administered to the patient, which administration may influence a sensed value of the monitored physiological parameter of the patient and thus may cause potential health threats for the monitored patient. Accordingly, the safety of the monitored patient may be guaranteed for those treatment conditions which may endanger the health state of the monitored patient. Further, unnecessary disturbances of a caregiver of the patient which may be caused by nuisance alarm signals generated in cases in which no supplementary treatment may be administered to the patient may be prevented. Further, in cases in which a caregiver of the patient may have manually set the alarm limit in the deactivated state and may have forgotten to reactivate the alarm limit as a treatment may be now administered to the patient, the controlling device may automatically account for the changed treatment condition of the patient, thereby increasing a safety of the patient.

The controlling unit may be configured for controlling the state of the alarm limit in a timely limited way (particularly for a predetermined time period). In particular, the controlling unit may be configured to automatically set the state of the alarm limit of the alarm device in a (default) state associated with a time prior to the executed controlling or in an additional state being defined by a caregiver prior to the executed controlling. In particular, the caregiver may define a particular value of the alarm limit to which the alarm limit may be set after the timely controlling. In particular, this defined value may be different from the (original) value of the alarm limit before the executed controlling. Accordingly, the controlled alarm limit may fall back after a time period into the previous state of the alarm limit which may be associated with a status in which (it may be assumed that) the treatment may not be administered to the patient. In particular, the time period after which the controlling may be finished may be selected according to a time scheme of an execution of the administering of the treatment to the patient. Thus, this kind of controlling may account for a timely limited administration of a treatment to the patient. In particular, combining this measure with the information being manually inputted into a respective device may avoid a generation of nuisance alarms during an administration of the treatment to the patient and meanwhile may not compromise a safety of the patient by ensuring that a particularly time-limited treatment administered to the patient may not cause the alarm limit to be permanently controlled in case the caregiver of the patient may forget to manually input further information whether a treatment may be administered to the patient or may re-control (particularly re-activate) the alarm limit of the alarm device.

The controlling unit may be configured for controlling at least one of a display of an indication indicating the state of the alarm limit and a display of an indication indicating whether the treatment may be administered to the patient. Thus, an additional, manually controllable supervision of the state of the alarm limit as well as of the treatment condition of the patient by a caregiver of the patient may be provided such that a caregiver of the patient may be able to personally control the state of the alarm limit of the patient, in order to check a proper operation of the controlling device.

In particular, the controlling of the display of the indication indicating the state of the alarm limit may be based on controlling of displaying or not displaying an indication indicating the value of the alarm limit and/or on controlling of displaying an additional (particularly text-based) indication comprising, for example, the content "Activated state" or "Deactivated state".

In particular, the controlling of the display of the indication whether the treatment may be administered to the patient may be based on controlling of displaying a (particularly text-based) indication comprising the content "Supplementary treatment" and "No supplementary treatment". In particular, the controlling of the display of the indication indicating whether the treatment may be administered to the patient may be based on controlling a display of a color of an indication indicating a monitored value of the physiological parameter, wherein a first color may correspond to the treatment being administered to the patient, and a second color may correspond to the treatment being not administered to the patient. For example, the first color may be a regularly used color when displaying the sensed value of the physiological parameter, and the second color may be red.

In particular, the controlling unit may be configured for controlling the display of the indication indicating the state of the alarm limit and the display of the indication indicating whether the treatment may be administered to the patient simultaneously or (particularly immediately) subsequently to the controlling of the state of the alarm limit. Thus, the display of the indication indicating the state of the alarm limit and the indication indicating whether the treatment may be administered to the patient may always correspond to the actual state of the alarm limit and the actual treatment condition of the patient, respectively.

In particular, the controlling device may comprise a respective display unit and/or may be connectable to a display unit of a patient monitoring apparatus and/or of a respective central surveillance system particularly comprising the patient monitoring apparatus, wherein the controlling unit may be configured for controlling a display of at least one of the latter mentioned display devices.

In particular, in order to control the display of at least one of the indication indicating the state of the alarm limit and the display of the indication indicating whether the treatment may be administered to the patient, the controlling unit may be configured for generating respective control signals for at least one of the latter mentioned display devices.

In particular, additionally or alternatively, the controlling unit may be configured for controlling at least one of an audio notification notifying the state of the alarm limit and a notification of an indication indicating whether the treatment may be administered to the patient in an audible way.

The physiological parameter of the patient may comprise a (arterial) hemoglobin oxygen saturation (SpO2) of the patient (particularly measured in units of fractions of 1 or in percentage or "%"), an oxygen partial pressure (pO2) of the patient (particularly measured in units of "mmHg"), a transcutaneously measured oxygen partial pressure (tpO2) of the patient (particularly measured in units of "mmHg"), a (particularly invasively monitored arterial) blood pressure of the patient (particularly measured in units of "mmHg"), a heart rate of the patient (particularly measured in units of beats per minute (BMP)), a pulse rate of the patient (particularly measured in units of impulses per minute), a respiratory rate of the patient (particularly measured in units of respiration acts per minute or second), a respiratory interval of the patient, a capnography parameter of the patient (particularly a concentration of carbon dioxide (CO2) in the respiratory gas measured in units of fractions of 1 or in percentage or a partial pressure of carbon dioxide (CO2) in the respiratory gas measured in units of "mmHg" or Pascal), or a (body) temperature of the patient (particularly measured in units of degree Celsius). These parameters may correspond to conventionally monitored physiological parameters of hospitalized patients in intensive care units, floor units or step-down units of a hospital, thereby the controlling device and the patient monitoring apparatus being versatile usable.

The treatment may comprise a treatment agent which may be supplied to the patient. Here, the term "treatment agent" may particularly denote a gaseous, fluid, or solid agent or a mixture of a gaseous, fluid and/or solid supplementary agent(s) supplied to a patient. In particular, supplying a treatment agent to a patient may impact, particularly increase or decrease, a sensed value of a monitored physiological parameter, thereby triggering a generation of an alarm signal by the alarm device.

The treatment agent may comprise supplementary oxygen or a vasodilatation drug. In particular, in a case of monitoring hemoglobin oxygen saturation, an oxygen partial pressure or a transcutaneously measured oxygen partial pressure of a patient, the treatment agent may correspond to supplementary oxygen, whereas, when monitoring a blood pressure of the patient, the treatment agent may correspond to a vasodilatation drug. These commonly used treatment agents may precisely indicate a potential health risk of the monitored patient.

In particular, the information indicating the supply of supplementary oxygen may comprise a "fraction of inspired oxygen" (FiO2) of a gaseous mixture or a respective value thereof which may be particularly measured in units of fractions of 1 or in percentage or "%". In particular, a FiO2 value corresponding to room air may be 0.21 or 21%. In particular, the respective FiO2 indication indicating the supply of the supplementary oxygen may comprise the particular value or the content "Supplementary oxygen" or "Room air". In particular, the respective threshold value usable during the determination whether the treatment agent may be supplied to the patient may correspond to a value of (about) 0.21 (corresponding to (about) 21%) being (approximately) equal to a regular amount of oxygen in room air.

In particular, additionally or alternatively, the information indicating the supply of supplementary oxygen may comprise a tidal volume, a minute volume, and a respiration rate.

The treatment may comprise a treatment procedure which may be applied to the patient. Here, the term "treatment procedure" may particularly denote electrical, electromagnetic, radioactive, light, mechanical, pneumatic or hydraulic energy applied to the patient for therapeutic reasons. In particular, applying a treatment procedure on a patient may impact, particularly increase or decrease, a sensed value of the monitored physiological parameter, thereby triggering the generation of the alarm signal by the alarm device.

The treatment procedure may comprise a ventilation, an electro-surgery (for example, electrical cauterization of tissue using an electro-surgery unit (ESU)), (transcutaneous) pacing, intra-aortic pumping (particularly using an intra-aortic balloon pump), suction of an airway of a patient, or therapeutic cooling. In particular, applying ventilation on a patient may impact a respiration of the patient and may thus be associated with a respiration alarm, an apnea alarm or a respiratory rate alarm. In particular, applying electro-surgery or pacing on a patient may impact a heart rate of the patient and may thus be associated with a heart rate alarm. In particular, applying an intra-aortic pumping on a patient may impact a pulse rate of the patient and may thus be associated with a pulse rate alarm. In particular, applying a therapeutic cooling on the patient (also referred to as "Induced Hypothermia") may impact a (body) temperature of the patient and may thus be associated with a (body) temperature alarm. In particular, applying airway suction on a patient may impact a hemoglobin oxygen saturation of the patient, a carbon dioxide (CO2) content of a blood of the patient, a respiration of the patient and may thus be associated with the SpO2 alarm, a CO2 alarm, or a respiration alarm. In this example, a lower alarm limit of the SpO2 alarm, a CO2 alarm, or a respiration alarm may be decreased or extended but not be set in a deactivated state.

In particular, in a case of monitoring a hemoglobin oxygen saturation of the patient and applying airway suction on the patient, the value of the lower SpO2 alarm limit, and/or the value of the lower CO2 alarm limit may be decreased. In particular, in a case of monitoring a (body) temperature of the patient and applying therapeutic cooling on the patient, the value of the lower and upper (body) temperature alarm limits may be decreased. Here, the respective values may be particularly selected based on a set point of cooling temperature. In particular, in a case of monitoring hemoglobin oxygen saturation of the patient, a CO2 content of a patient blood, or a respiration of the patient, and applying airway suction on the patient, the value of the lower SpO2 alarm limit, the value of the lower respiration rate alarm limit, or the value of CO2 alarm limit may be decreased.

In particular, the receiving unit may be configured for anew receiving information indicating an administration of a treatment to the patient, the determining unit may be configured for anew determining whether the treatment may be administered to the patient based on the received information, and the controlling unit may be configured for anew controlling the state of the alarm limit based on a result of the determination of the determining unit. Thus, the controlling device may be configured for continuously controlling of the state of the alarm limit.

In particular, the controlling device may form part of a patient monitoring apparatus or may represent an individual module being connectable to various (particularly different) kinds of patient monitoring apparatuses, thus representing a retrofitting module for an already existing patient monitoring apparatus.

In particular, suitable embodiments of at least one of the receiving unit, the determining unit, and the controlling unit may correspond to one or more processors comprising integrated circuits having suitable electronic components such as power supply units, diodes, transistors, integrators, and/or logical components such as AND-, OR-, or NOR-gates. In particular, the receiving unit may be embodied as an interface module or an Input/output-port of a processor.

Next, further exemplary embodiments of the patient monitoring apparatus for monitoring a physiological parameter of a patient will be explained. However, these embodiments also apply to the respective controlling device, the respective method, the respective computer-readable medium, and the respective program element.

In particular, the patient monitoring apparatus may be connectable to a sensing device (or more sensing devices) configured for sensing a value of the (more) physiological parameter(s) of the patient, wherein the alarm device may be configured for generating the alarm signal based on the sensed value(s). Thus, the patient monitoring apparatus may be usable in association with monitoring various physiological parameters.

In particular, alternatively or additionally, the patient monitoring apparatus may further comprise a sensing device configured for sensing a value of the physiological parameter of the patient, wherein the alarm device may be configured for generating the alarm signal based on the sensed value. Such a patient monitoring apparatus may represent a self-contained apparatus being installable in various kinds of treatment environments without the need of further devices.

The patient monitoring apparatus may further comprise a display device configured for at least one of displaying an indication indicating the state of the alarm limit, and for displaying an indication indicating whether the treatment may be administered to the patient. Thus, a visualization of parameters relevant for the health state of the patient may be provided particularly to the caregiver of the patient, thereby the caregiver being able to additionally personally control a proper operation of the control device and the patient monitoring apparatus. Thus, the safety of the patient during the monitoring may be increased.

The patient monitoring apparatus may be connectable to another display device configured for at least one of displaying an indication indicating the state of the alarm limit, and for displaying an indication indicating whether the treatment is administered to the patient. Such a display device may represent a remote display device of a central surveillance system which may particularly comprise a plurality of patient monitoring apparatuses.

The patient monitoring apparatus may further comprise or may be connectable to another sensing device configured for sensing a value of the treatment administered to the patient. Thus, the patient monitoring apparatus may represent a self-contained system which may not rely on supplementary information provided by further devices.

BRIEF DESCRIPTION OF THE DRAWINGS

The invention will be described in more detail hereinafter with reference to examples of embodiment but to which the invention is not limited.

DETAILED DESCRIPTION OF EMBODIMENTS

Figure 1:
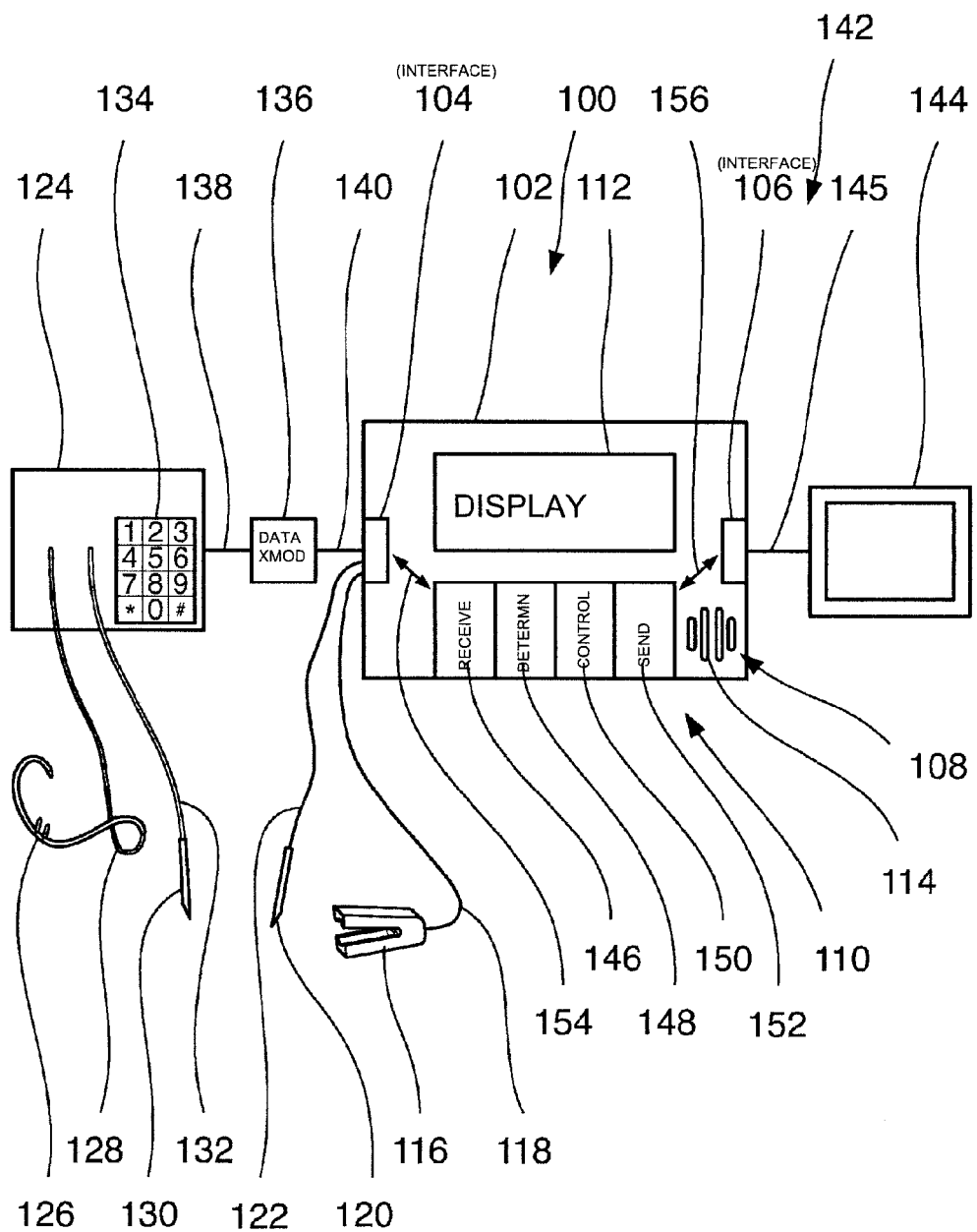
FIG. 1 shows a patient monitoring apparatus according to an exemplary embodiment of the invention.

The illustration in the drawing is schematic. It is noted that in different Figures, similar or identical elements are provided with the same reference signs or with reference signs, which are different from the corresponding reference signs only with a first digit.

FIG. 1 shows a patient monitoring apparatus 100 according to an exemplary embodiment of the invention. The patient monitoring apparatus 100 is used for monitoring the arterial oxygen saturation of a preterm infant and for invasively monitoring an arterial blood pressure of the preterm infant. The patient monitoring apparatus 100 is configured as IntelliVue™ Patient Monitor manufactured by Philips™ and is installable in a Neonatal Intensive Care Unit of a hospital. The patient monitoring apparatus 100 comprises a housing 102, in which two interfaces 104, 106, an alarm device 108 configured for generating an alarm signal in association with the monitored arterial oxygen saturation and the arterial blood pressure of the infant, a controlling device 110 configured for controlling a state of alarm limits of the alarm device 108, and a display device 112 is accommodated.

The interfaces 104, 106 are configured for providing a connection to further electronic components.

The alarm device 108 comprises a loudspeaker 114 configured for announcing an alarm signal in response to a sensed arterial oxygen saturation value or a sensed arterial blood pressure value of the infant.

The alarm device 108 comprises lower and upper limits associated with the arterial oxygen saturation and the blood pressure such that a respective alarm signal is provided by alarm device 108 in cases in which the sensed values of the arterial oxygen saturation and the arterial blood pressure are lower or higher than the upper and lower limit values defined in the alarm device 108. The lower and upper alarm limits associated with the arterial hemoglobin oxygen saturation are 88% and 94%, and the lower and upper alarm limits associated with the arterial blood pressure are 65 and 110, respectively.

The display device 112 is configured for displaying a sensed value of the hemoglobin oxygen saturation, a sensed value of the arterial blood pressure, and the upper and lower alarm limit associated with the monitored arterial hemoglobin oxygen saturation and the alarm limits associated with the monitored arterial blood pressure. Further information which may be displayed by the display device 112, 144 will be explained with reference to FIG. 2.

A first sensing device 116 is configured for sensing the arterial oxygen saturation of the monitored infant and is connected to the interface 104 of the patient monitoring apparatus 100 via a first cable 118. The sensing device 116 is configured as a foot sensor forming part of a pulse oximetry device accommodated in the housing 102 of the patient monitoring apparatus 100. A second sensing device 120 is configured for invasively sensing the arterial blood pressure of the infant and is connected to the interface 104 of the patient monitoring apparatus 100 via a second cable 122. The sensing device 120 is configured as a hypodermic needle being accommodatable into an artery of the infant, connected to a pressure transducer via a fluid filled line. A respective blood pressure measuring device is accommodated in the housing 102 of the patient monitoring apparatus 100.

The patient monitoring apparatus 100 is further connectable to a treatment agent supply device 124 in the form of a combined ventilator and drug reservoir. The treatment agent supply device 124 is configured for supplying supplementary oxygen to the infant via a respiratory element 126 and a respective tube 128. An injection needle 130 is connected to the treatment agent supply device 124 via a tube 132 such that a vasodilatation drug is injectable in the body of the infant using titration techniques. Further, the treatment agent supply device 124 comprises a keyboard 134 via which an operator may input a value corresponding to an amount of supplied supplementary oxygen and an amount of the supplied vasodilatation drug.

The patient monitor apparatus 100 is connected via a module 136 to the treatment agent supply device 124 such that a data exchange between the treatment agent supply device 124 and the patient monitoring device 100 is mediated by the module 136. The module 136 is configured as a commercially available VueLink™ and/or IntelliBridge™ Interface Module manufactured by Philips™. In particular, information pertaining to whether supplementary oxygen is supplied to the infant and/or the inputted value of the amount of the vasodilatation drug supplied to the infant is transferable from the treatment agent supply device 124 to the interface 104 of the patient monitoring apparatus 100 via the module 136. The connection between the treatment agent supply device 124 and the module 136 and between the module 136 and the patient monitoring device 100 is accomplished via cables 138 and 140, respectively.

The patient monitoring apparatus 100 forms part of a central surveillance system 142 which comprises up to 16 patient monitoring apparatuses similar to the patient monitoring apparatus 100 and a central display device 144 arranged at a remote place, for example, in a nurses' room. The central display device 144 is connected to the interface 106 of the patient monitoring apparatus 100 via a cable 145 and the other patient monitoring apparatuses. The central surveillance system is configured as Philips™ Information Center (PIC).

Alternatively, a communication between the patient monitoring apparatus 100 and the display device 144 of the central surveillance system 142 may be based on a wireless communication.

In the following, the control device 110 of the patient monitoring apparatus 100 will be described in more detail.

The controlling device 110 is configured for controlling the state of the upper alarm limit of the alarm device 108 associated with the measured oxygen saturation and the upper and lower alarm limits of the alarm device 108 associated with the measured arterial blood pressure. The controlling device 110 comprises a receiving unit 146, a determining unit 148, a controlling unit 150, and a sending unit 152. A constructive implementation of the controlling device 110 may comprise integrated circuits having suitable electronic components accomplishing the functions of the individual units.

The receiving unit 146 is adapted for receiving a sensed value of the arterial hemoglobin oxygen saturation of the infant, a sensed value of the arterial blood pressure of the infant, an information containing the FiO2 value, and the indication indicating whether the vasodilatation drug is supplied to the infant or not. A connection between the receiving unit 146 and the interface 104 is wire-based and is indicated by the double-ended arrow 154.

The determining unit 148 is configured for determining whether the supplementary oxygen and/or the vasodilatation drug is supplied to the infant based on the information received from the receiving unit 146 using the following algorithms: When receiving a FiO2 value indicating the present amount or percentage of oxygen in the gaseous mixture supplied to the infant, the determining unit 148 is configured for determining that supplementary oxygen is supplied to the infant in case the value received from the treatment agent supply device 124 exceeds a predefined threshold value. Accordingly, in case the received value is below or is equal to the threshold value, the determining unit 148 is configured for determining that supplementary oxygen is not supplied to the infant. The threshold value is independent of the age of the infant and is selected to be 0.21. Further, in case the indication received from the treatment agent supply device 124 indicates that a vasodilatation drug is supplied to the infant, the determining unit is configured for determining that the vasodilatation drug is supplied to the infant. Accordingly, in case the indication received from the treatment agent supply device 124 indicates that no vasodilatation drug is supplied to the infant, the determining unit is configured for determining that the vasodilatation drug is not supplied to the infant. Instead of executing the latter described determination, the determining unit 148 may also simply process the received indication and passes suitable information, for example in a different format, to the controlling unit 150.

The controlling unit 150 is configured for executing the controlling of the state of the upper alarm limit of the alarm device 108 associated with the arterial oxygen saturation and the alarm limits of the alarm device 108 associated with the arterial blood pressure based on the result of the determination executed by the determination unit 148 and uses the following algorithms: In case the determination results in that supplementary oxygen is not supplied to the infant, i.e. the infant is exposed to regular air, the upper alarm limit associated with the oxygen saturation is set in its deactivated state by switching off the upper alarm limit. In case the determination results in that supplementary oxygen is supplied to the infant, i.e. the infant is exposed to a gaseous mixture having a FiO2 value higher than 0.21, the upper alarm limit is set in its activated state and thus to its predetermined value of 94% or the value that the caregiver previously had assigned.

The controlling of the upper alarm limit associated with the measured arterial blood pressure uses the following definitions: In case that the vasodilatation drug is supplied to the infant the alarm limits associated with the arterial blood pressure are both decreased in their value. In case that no vasodilatation drug is supplied to the infant the alarm limits associated with the arterial blood pressure of the infant are set to their predetermined values of 65 and 110, respectively, or the values that the caregiver previously had assigned.

Alternatively, the control unit 150 may be configured for setting the upper alarm limit associated with the arterial oxygen saturation to 100%, instead of switching off the upper alarm limit.

The sending unit 152 is configured for providing respective control signals to the alarm unit 114. A connection between the sending unit 152 and the interface 106 is wire-based and is indicated by the double-ended arrow 156.

Further, the controlling unit 150 is configured for generating control signals for controlling a display of the display device 144 of the central surveillance system 142 and the display device 112 of the patient monitoring apparatus 100 as will be explained with reference to FIG. 2. A connection between the sending unit 152 and the display device 112 is also wire-based.

In operation of the controlling device 110 and the patient monitoring apparatus 100, an infant is connected to the treatment agent supply device 124 via the respiratory element 126 and the hypodermic needle 130 and to the patient monitoring apparatus 100 via the sensing devices 116, 120. A caregiver of the infant inputs a numerical value of 0.21 into the keyboard 134 of the treatment agent supply device 124. Further, the caregiver inputs a value of 5 corresponding to an amount of 5 µg/kg/min of a vasodilatation drug to be supplied to the infant. Accordingly, no supplementary oxygen is supplied to the infant but an amount of 5 µg/kg/min of a vasodilatation drug.

The patient monitoring device 100 receives information about the monitored arterial blood pressure and the monitored arterial oxygen saturation from the sensing devices 116, 120. Further, the patient monitoring apparatus 100 may receive information about a tidal volume, a minute volume, and a respiration rate from the treatment agent supply device 124.

Further, the patient monitoring device 100 receives the information having the content "0.21" and the indication indicating that a vasodilatation drug is supplied to the infant via the module 136. Accordingly, the state of the upper alarm limit associated with the monitored arterial oxygen saturation and the alarm limits associated with the monitored arterial blood pressure is controlled by the controlling device 110 based on the received information. Here, the determination unit 148 determines that no supplementary oxygen is supplied to the infant but a vasodilatation drug is supplied to the infant. The controlling unit 150 sets the upper alarm limit associated with the arterial oxygen saturation of the infant in its deactivated state but sets the alarm limits associated with the arterial blood pressure of the infant to a lower range of 50 mmHg and 100 mmHg, respectively. Respective information about the supply of supplementary oxygen, the supply of the vasodilatation drug, the upper and lower alarm limits associated with the monitored oxygen saturation, and the monitored arterial blood pressure, the monitored oxygen saturation and the monitored arterial blood pressure are displayed by the display devices 112, 144.

Figure 2:
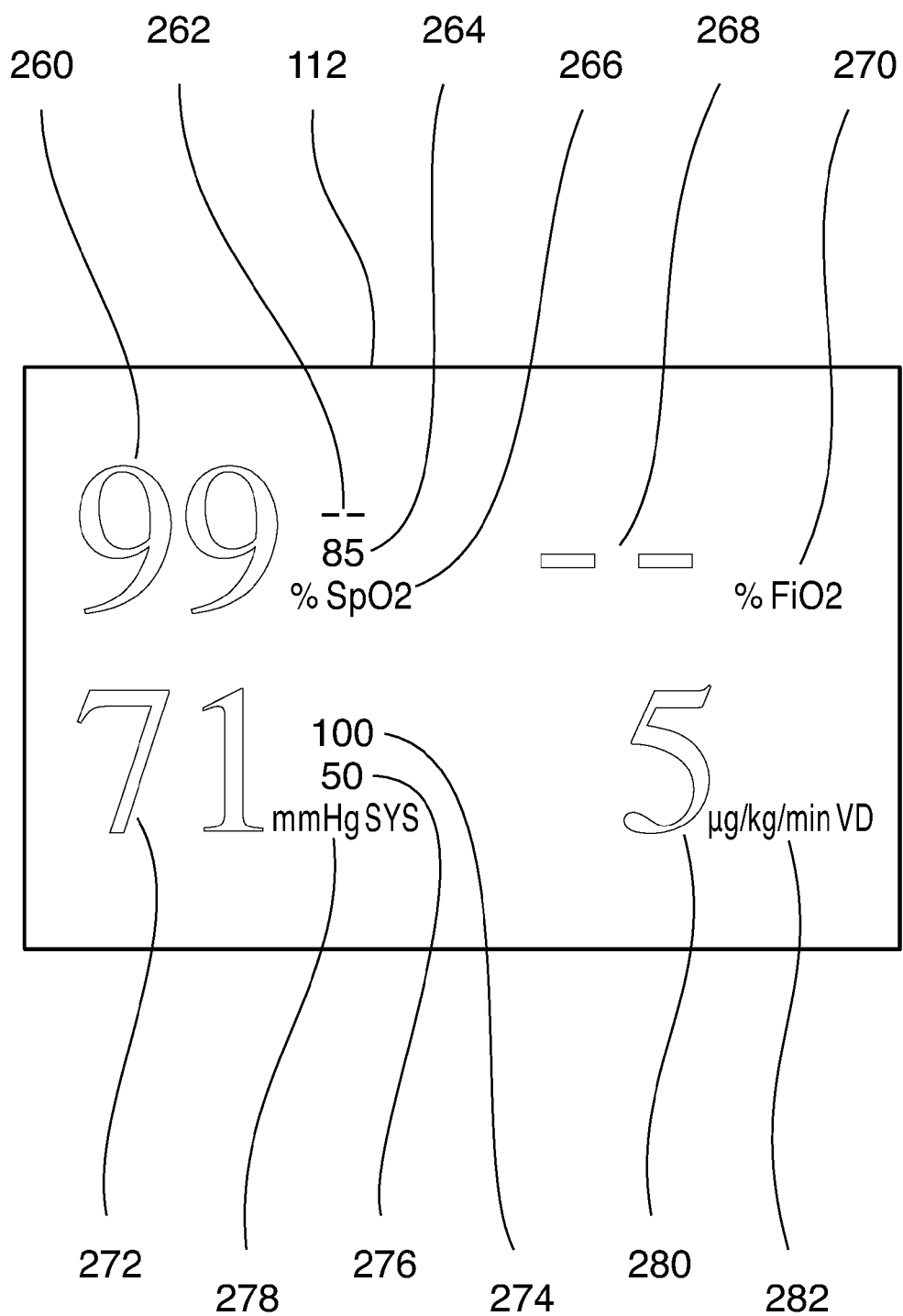
FIG. 2 shows a display provided by a display unit of the patient monitoring apparatus of FIG. 1

Referring to FIG. 2, a display of the display device 112 will be explained in more detail. This content displayed by the display device 112 and the content displayed by the display device 144 are identical to one another.

The display unit 112 is adapted to display an indication 260 indicating the sensed arterial oxygen saturation value, an indication 262 indicating the state and/or value of the upper alarm limit associated with the oxygen saturation of the infant, an indication 264 indicating the state and/or value of the lower limit of the alarm associated with the oxygen saturation of the infant, and a label indication 266 indicating the kind of displayed information and its unit. The latter described indications 260-266 correspond to "99", "- -", "85", and "% SpO2". Hence, since the upper alarm limit is set in a deactivated state, the indication 262 only indicates the deactivated state by not displaying the value but does not indicate the value of the upper alarm limit.

Further, the display comprises an indication 268 indicating the amount of supplementary oxygen supplied to the infant and a respective label indication 270 indicating the kind and unit of displayed information. As no supplementary oxygen is supplied to the infant, the displayed indication 268 is "- -".

Further, the display comprises an indication 272 indicating the value of the sensed arterial blood pressure (in the shown embodiment "71"), an indication 274 indicating a value of the upper alarm limit associated with the arterial blood pressure (here "100"), an indication 276 indicating a value of the lower alarm limit associated with the arterial blood pressure ("50"), and a label indication 278 indicating the kind and unit of displayed information ("mmHg SYS").

The display also comprises an indication 280 indicating the amount of the supplied vasodilatation drug ("5"), and a respective label indication 282 ("μg/kg/min VD") denoting the kind and unit of displayed information of the indication 280.

Alternatively, instead of displaying or not displaying the indications 268, 270, 280, 282, the color of the indication 260, 272 may be controlled by the controlling unit 112 in that a first color, for example red, may correspond to the fact that supplementary oxygen is supplied to the infant, and a second color, for example black, may correspond to the fact that no supplementary oxygen is supplied to the infant.

Alternatively, instead of displaying the FiO2 value or value indicating the amount of the vasodilatation drug, a simple indication in the form of a text "NO" or "YES", "Room air" and "Supplementary oxygen" or "Vasodilatation drug" and "No vasodilatation drug" may be displayed.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the use of the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A controlling device for controlling a state of an alarm limit of an alarm device, wherein the alarm device is configured for generating an alarm signal in association with a monitored physiological parameter of a patient, wherein the alarm limit triggers the generation of the alarm signal, the controlling device comprising:
a receiving unit configured for receiving information indicating an administration of a treatment to the patient,
a determining unit configured for determining whether the treatment is administered to the patient based on the information received from the receiving unit, and
a controlling unit configured for changing at least one of an operational mode of the alarm limit and a value of the alarm limit based on a result determined by the determining unit.

2. The controlling device according to claim 1, wherein the controlling unit is configured to control the value of the alarm limit by changing at least one of a lower alarm limit value of the alarm device and an upper alarm limit value of the alarm device in response to the determining unit determining that a treatment is being administered to the patient.

3. The controlling device according to claim 1, wherein the information comprises at least one of an indication indicating whether the treatment is currently being administered to the patient, and a value of a monitored physiological parameter indicating that the treatment administered to the patient.

4. The controlling device according to claim 3, wherein the determining unit is configured for comparing the value of the monitored physiological parameter value with a threshold value, wherein the determining unit is configured for determining whether the treatment is being administered to the patient based on the comparison.

5. The controlling device according to claim 1, wherein the controlling unit is configured for controlling the operational mode of the alarm limit to one of an activated state and a deactivated state based on a result of the determining unit determining that treatment is being administered.

6. The controlling device according to claim 1, wherein the controlling unit is configured for, in response to the determining unit determining that treatment is being administered, controlling a display device to display an indication indicating that the treatment is being administered to the patient.

7. The controlling device according to claim 3, wherein the monitored physiological parameter comprises one or more of a hemoglobin oxygen saturation of the patient, a transcutaneously measured oxygen partial pressure of the patient, a blood pressure of the patient, a heart rate of the patient, a pulse rate of the patient, a respiratory rate of the patient, a respiratory interval of the patient, a capnography parameter of the patient, and a temperature of the patient.

8. The controlling device according to claim 1, wherein the treatment comprises administering a treatment agent to the patient.

9. The controlling device according to claim 8, wherein the treatment agent comprises at least one of supplementary oxygen and a vasodilatation drug.

10. The controlling device according to claim 1, wherein the treatment comprises one or more of a ventilation, an electro-surgery, a pacing, an intra-aortic pumping, a suction of an airway of a patient, and a therapeutic cooling.

11. A patient monitoring apparatus for monitoring a physiological parameter of a patient, the patient monitoring apparatus comprising:
an alarm device configured for generating an alarm signal in association with the monitored physiological parameter of the patient, and
a controlling device configured for controlling the state of the alarm limit of the alarm device according to claim 1.

12. The patient monitoring apparatus according to claim 11, the patient monitoring apparatus further comprising:
a display device configured for at least one of displaying an indication indicating whether the treatment is administered to the patient.

13. A patient monitoring apparatus for monitoring at least one physiological parameter of a patient, the apparatus comprising:
one or more processors configured to:
receive values of monitored physiological parameters,
determine whether the values of the received physiological parameters violates alarm limits,
determine whether a treatment administering apparatus is administering a treatment to the patient, and in response to determining that the treatment is being administered to the patient, change at least one of an operational mode and a value of an alarm limit.

14. The apparatus according to claim 13, wherein the one or more processors configured to:
determine whether a treatment apparatus is administering treatment to the patient based on the received values of the monitored physiological parameters.

15. The apparatus according to claim 14, further including:
physiological parameter sensing devices configured to monitor physiological parameters of the patient and supply the values of the monitored physiological parameters to the one or more processors.

16. The apparatus according to claim 13, further including:
a treatment agent supply device configured to administer a liquid or gaseous treatment agent to the patient, the treatment administration apparatus providing information to the one or more processors from which the one or more processors are configured to determine whether the treatment administration apparatus is administering the treatment.

17. The apparatus according to claim 13, further including:
a display device, the display device being configured to indicate whether the treatment is being administered by the treatment administering apparatus to the patient.

18. A patient monitoring apparatus for monitoring at least one physiological parameter of a patient, the apparatus comprising:
one or more processors configured to:
receive values of monitored physiological parameters,
determine whether the values of the received physiological parameters violates alarm limits,
determine whether a treatment administering apparatus is administering a treatment to the patient, and
in response to determining that the treatment is being administered to the patient, change at least one of an operational mode and a value of an alarm limit; and
a display device, the display device being configured to indicate whether the treatment is being administered by the treatment administering apparatus to the patient;
wherein the display device is further configured to display one or more values of the monitored physiological parameters and indicate when the values of the received physiological parameters violate the alarm limits.

19. A method for monitoring physiological parameters of a patient, the method comprising:
with one or more processors, receiving values of monitored physiological parameters;
with the one or more processors, determining whether the values of the received physiological parameters violates alarm limits;
with the one or more processors, determining whether a treatment administering apparatus is administering a treatment to the patient; and
with the one or more processors, in response to determining that the treatment is being administered to the patient, changing at least one of an operational mode and a value of the alarm limits.

20. The method according to claim 19, wherein one or more of the alarm limits is changed in response to the determination that the treatment is being administered.

* * * * *